US008440618B2

(12) United States Patent
Maher et al.

(10) Patent No.: US 8,440,618 B2
(45) Date of Patent: May 14, 2013

(54) COMPOSITION FOR THE ATTACHMENT OF IMPLANTS TO COLLAGEN OR OTHER COMPONENTS OF BIOLOGICAL TISSUE

(75) Inventors: Suzanne A. Maher, Highland Lakes, NJ (US); Jeffrey Schwartz, Princeton, NJ (US); Axel Oscar Magnus Hook, Houston, TX (US); Brooke Hageman Russell, Pearland, TX (US); Casey Marie Jones, Portland, OR (US)

(73) Assignees: New York Society for the Ruptured and Crippled Maintaining the Hospital for Special Surgery, New York, NY (US); The Trustees of Princeton University, Princeton, NJ (US); The Texas A&M University System, College Station, TX (US)

( * ) Notice: Subject to any disclaimer, the term of this patent is extended or adjusted under 35 U.S.C. 154(b) by 0 days.

(21) Appl. No.: 13/353,952

(22) Filed: Jan. 19, 2012

(65) Prior Publication Data

US 2012/0208758 A1    Aug. 16, 2012

Related U.S. Application Data

(60) Provisional application No. 61/434,144, filed on Jan. 19, 2011.

(51) Int. Cl.
| | | |
|---|---|---|
| *A61K 38/36* | (2006.01) | |
| *A61P 7/04* | (2006.01) | |
| *C07K 14/75* | (2006.01) | |
| *C07K 14/475* | (2006.01) | |

(52) U.S. Cl.
USPC .......... 514/13.6; 424/422; 424/423; 424/548; 514/17.1; 523/113

(58) Field of Classification Search ....................... None
See application file for complete search history.

(56) References Cited

U.S. PATENT DOCUMENTS

| 2002/0111694 | A1 | 8/2002 | Ellingsen et al. | |
| 2006/0160734 | A1* | 7/2006 | Kusanagi et al. | 514/12 |
| 2011/0184529 | A1* | 7/2011 | Forsgren et al. | 623/23.53 |

FOREIGN PATENT DOCUMENTS

| WO | WO 96/10428 | 4/1996 |
| WO | WO 9743314 A2 * | 11/1997 |
| WO | WO 2006102457 A2 * | 9/2006 |
| WO | WO 2007022188 A2 * | 2/2007 |

OTHER PUBLICATIONS

Busscher H et al "Intermolecular Forces and Enthalpies in the Adhesion of *Streptococcus mutans* and an Antigen I/II-deficient mutant to Laminin Films" J Bacteriology 189:2988-2995. Published Feb. 2, 2007.*

Bussolino F et al "Angiogenesis: a balancing act between integrin activation and inhibition?" Eur. Cytokine Netw. 20:191-196. Published Dec. 2009.*
Ferdous Z et al "A role for decorin in controlling proliferation, adhesion, and migration of murine embryonic fibroblasts" J of Biomed Materials Research Part A 93:419-428. Published May 2010.*
Rich R et al "Trench-shaped Binding Sites Promote Multiple Classes of Interactions between Collagen and the Adherence Receptors, a1/b1 Integrin and *Staphylococcus aureus* Cna MSCRAMM" J Biol Chem 274:24906-24913. Published Aug. 27, 1999.*
Charlton D et al "Semi-Degradable Scaffold for Articular Cartilage Replacment" Tissue Engineering: Part A 14:207-213. Published 2008.*
Spiller K et al "Superporous hydrogels for cartilage repair: Evaluation of the morphological and mechanical properties" Acta Biomaterialia 4:17-25. Published Sep. 22, 2007.*
Bierbaum S et al "Collagenous matrix coatings on titanium implants modified with decorin and chondroitin sulfate: Characterization and influences on osteoblastic cells" J Biomed Materials Research Part A 77:551-62. Published Jun. 1, 2006.*
Shankari N. Somayaji et al. "UV-killed *Staphlococcus aureau* Enhances Adhesion and Differentiation of Osteoblasts on Bone-associated Biomaterials", J Biomed Mater Res A., Nov. 2010; 95(2):pp. 574-979. Retrieved from the Internet: doi: 10.1002/jbm.a. 32890, abstract, p. 2, 5, 6, 7.
Leslie I. Gold et al., Fibronectin-Collagen Binding and Requirement during Cellular Adhesion, Biochem J., Feb. 15, 1980; 186(2):pp. 551-559, especially, abstract, p. 551, right col., p. 552, left col.
Adina-Elena Segneanu et al., Reactive organic carbonates with leaving group for biologically active dipeptides synthesis, Environmental Engineering and Management Journal, Jul./Aug. 2009, vol. 8, No. 4, pp. 797-801, especially, abstract.
Buckwalter JA, Mankin HJ. Articular cartilage: degeneration and osteoarthritis, repair, regeneration, and transplantation. *Instr Course Lect* 1998;47:487-504.
Woolf AD, Pfleger B. Burden of major musculoskeletal conditions. *Bull World Health Organ* 2003;81(9):646-56.
Gelber A, Hochberg M, Mead L, Wang N, Wigley F, Klag M. Joint injury in young adults and risk for subsequent knee and hip osteoarthritis. *Ann Intern Med* 2000;133(5):321-328.
Maher et al. Nondegradable Hydrogels for the Treatment of Focal Cartilage Defects, *J Biomed Mater Res* 2007;83(A):145.
Szerb et al. Mosaicplasty: Long-term Follow-up, *Bull Hosp. Jt. Dis.* 2005;56:54.
Freedman et al. Marrow Stimulation Technique to Augment Meniscus Repair, *Arthroscopy* 2003;19:794.
Brittberg et al. Articular Cartilage Engineering with Autologous Chrondrocyte Transplantation: A Review of Recent Developments, *J. Bone Joint Surg Am* 2003;85(Supp3): 109.
Gross Cartilage Resurfacing: Filling Defects, *J. Arthroplasty* 2003;18 (3 Suppl.1):14.
Lane JG, Healey RM, Chen AC, Sah RL, Amiel D. Can osteochondral grafting be augmented with microfracture in an extended-size lesion of articular cartilage? *Am J Sports Med* 2010;38(7):1316-23.

(Continued)

*Primary Examiner* — Cecilia J Tsang
*Assistant Examiner* — Zachary J Miknis
(74) *Attorney, Agent, or Firm* — Leason Ellis LLP

(57) ABSTRACT

The present invention relates to a novel composition comprising an implant, scaffold or construct bound to a biological or chemical moiety. The bound moiety has the ability to bind to a component of the extracellular matrix of biological tissue, allowing the implant to be bound to the biological tissue in a short period of time after implantation. The invention also relates to the use and manufacture of this novel composition, as well as a novel use for the protein CNA.

19 Claims, 6 Drawing Sheets

OTHER PUBLICATIONS

Fortier LA, Potter HG, Rickey EJ, Schnabel LV, Foo LF, Chong LR, Stokol T, Cheetham J, Nixon AJ. Concentrated bone marrow aspirate improves full-thickness cartilage repair compared with microfracture in the equine model. *J Bone Joint Surg Am* 2010;92(10):1927-37.

Gill TJ, McCulloch PC, Glasson SS, Blanchet T, Morris EA. Chondral defect repair after the microfracture procedure: a nonhuman primate model. *Am J Sports Med* 2005;33(5):680-5.

Hoemann CD, Hurtig M, Rossomacha E, Sun J, Chevrier A, Shive MS, Buschmann MD. Chitosan-glycerol phosphate/blood implants improve hyaline cartilage repair in ovine microfracture defects. *J Bone Joint Surg Am* 2005;87(12):2671-86.

Watanabe A, Boesch C, Anderson SE, Brehm W, Mainil Varlet P. Ability of dGEMRIC and T2 mapping to evaluate cartilage repair after microfracture: a goat study. *Osteoarthritis Cartilage* 2009;17(10):1341-9.

Hattori K, Uematsu K, Matsumori H, Dohi Y, Takakura Y, Ohgushi H. Spectrocolorimetric evaluation of repaired articular cartilage after a microfracture. *BMC Res Notes* 2008;1:87.

LaPrade RF, Bursch LS, Olson EJ, Havlas V, Carlson CS. Histologic and immunohistochemical characteristics of failed articular cartilage resurfacing procedures for osteochondritis of the knee: a case series. *Am J Sports Med* 2008;36(2):360-8.

Morisset S, Frisbie DD, Robbins PD, Nixon AJ, McIlwraith CW. IL-1/IGF-1 gene therapy modulates repair of microfractured chondral defects. *Clin Orthop Relat Res* 2007;462:221-8.

Kreuz PC, Steinwachs MR, Erggelet C, Krause SJ, Konrad G, Uhl M, Südkamp N. Results after microfracture of full-thickness chondral defects in different compartments in the knee. *Osteoarthritis Cartilage* 2006;14(11):1119-25.

Bobić V. Arthroscopic osteochondral autograft transplantation in anterior cruciate ligament reconstruction: a preliminary clinical study. *Knee Surg Sports Traumatol Arthrosc* 1996;3(4):262-4.

Hangody L, Kish G, Kárpáti Z, Udvarheyli I, Szigeti I, Bély M. Mosaicplasty for the treatment of articular cartilage defects: application in clinical practice. *Orthopedics* 1998;21(7):751-6.

Evans PJ, Miniaci A, Hurtig MB. Manual punch versus power harvesting of osteochondral grafts. *Arthroscopy* 2004;20(3):306-10.

Zhang Z, McCaffery JM, Spencer RG, Francomano CA. Growth and integration of neocartilage with native cartilage in vitro. *J Orthop Res* 2005;23(2):433-9.

Hunziker EB, Quinn TM. Surgical removal of articular cartilage leads to loss of chondrocytes from cartilage bordering the wound edge. *J Bone Joint Surg Am* 2003;85-A Suppl 2:85-92.

Enders JT, Otto TJ, Peters HC, Wu J, Hardouin S, Moed BR, Zhang Z. A model for studying human articular cartilage integration in vitro. *J Biomed Mater Res A* 2010;94(2):509-14.

Kock N, van Susante J, Wymenga A, Buma P. Histological evaluation of a mosaicplasty of the femoral condyle-retrieval specimens obtained after total knee arthroplasty—a case report. *Acta Orthop Scand* 2004;75(4):505-8.

Lane JG, Massie JB, Ball ST, Amiel ME, Chen AC, Bae WC, Sah RL, Amiel D. Follow-up of osteochondral plug transfers in a goat model: a 6-month study. *Am J Sports Med* 2004;32(6):1440-50.

Williams RJ, Ranawat AS, Potter HG, Carter T, Warren RF. Fresh stored allografts for the treatment of osteochondral defects of the knee. *J Bone Joint Surg Am* 2007;89(4):718-26.

Marquass B, Somerson JS, Hepp P, Aigner T, Schwan S, Bader A, Josten C, Zschamack M, Schulz RM. A novel MSC-seeded triphasic construct for the repair of osteochondral defects. *J Orthop Res* 2010;28(12):1586-99.

Solheim E, Hegna J, Oyen J, Austgulen OK, Harlem T, Strand T. Osteochondral autografting (mosaicplasty) in articular cartilage defects in the knee: results at 5 to 9 years. *Knee* 2010;17(1):84-7.

Schaefer D, Martin I, Jundt G, et al. Tissue-engineered composites for the repair of large osteochondral defects. *Arthritis Rheum* 2002;46(9):2524-34.

Niederauer GG, Slivka MA, Leatherbury NC, et al. Evaluation of multiphase implants for repair of focal osteochondral defects in goats. *Biomaterials* 2000;21(24):2561-74.

Wegener B, Schrimpf FM, Bergschmidt P, et al. Cartilage regeneration by bone marrow cells-seeded scaffolds. *J Biomed Mater Res A* 2010;95(3):735-40.

Nehrer S, Breinan HA, Ramappa A, et al. Chondrocyte-seeded collagen matrices implanted in a chondral defect in a canine model. *Biomaterials* 1998;19(24):2313-28.

Jiang CC, Chiang H, Liao CJ, et al. Repair of porcine articular cartilage defect with a biphasic osteochondral composite. *J Orthop Res* 2007;25(10):1277-90.

Ito Y, Ochi M, Adachi N, et al. Repair of osteochondral defect with tissue-engineered chondral plug in a rabbit model. *Arthroscopy* 2005;21(10):1155-63.

Wang W, Li B, Li Y, et al. In vivo restoration of full-thickness cartilage defects by poly(lactide-co-glycolide) sponges filled with fibrin gel, bone marrow mesenchymal stem cells and DNA complexes. *Biomaterials* 2010;31(23):5953-65.

Obradovic B, Martin I, Padera RF, et al. Integration of engineered cartilage. *J Orthop Res* 2001;19(6):1089-97.

Hunziker EB, Kapfinger E. Removal of proteoglycans from the surface of defects in articular cartilage transiently enhances coverage by repair cells. *J Bone Joint Stag Br* 1998;80(1):144-50.

Pabbruwe MB, Esfandiari E, Kafienah W, Tarlton JF, Hollander AP. Induction of cartilage integration by a chondrocyte/collagen-scaffold implant. *Biomaterials* 2009; 30(26):4277-86.

Fortier LA, et al. Insulin-like growth factor-1 enhances cell-based repair of articular cartilage. *J Bone Joint Surg Br* 2002;84(2):276-88.

Sellers RS, Zhang R, Glasson SS, et al. Repair of articular cartilage defects one year after treatment with recombinant human bone morphogenetic protein-2 (rhBMP-2). *J Bone Joint Surg Am* 2000;82(2):151-60.

Wang DA, Varghese S, Sharma B, Strehin I, Fermanian S, Gorham J, Fairbrother DH, Cascio B, Elisseeff JH. Multifunctional chondroitin sulphate for cartilage tissue biomaterial integration. *Nat Mater* 2007; 6(5):385-92.

Strehin I, Nahas Z, Arora K, Nguyen T, Elisseeff J. A versatile pH sensitive chondroitin sulfate-PEG tissue adhesive and hydrogel. *Biomaterials* 2010; 31(10):2788-97.

Mohamed N, Teeters MA, Patti JM, Höök M, Ross JM. Inhibition of *Staphylococcus aureus* adherence to collagen under dynamic conditions. *Infect Immun.* 1999;67(2):589-94.

Switalski LM, Speziale P, Höök M. Isolation and characterization of a putative collagen receptor from *Staphylococcus aureus* strain Cowan 1. *JBiol Chem.* 1989;264(35):21080-6.

Patti JM, Jonsson H, Guss B, Switalski LM, Wiberg K, Lindberg M, Höök M. Molecular characterization and expression of a gene encoding a *Staphylococcus aureus* collagen adhesion. *J Biol Chem.* 1992;267(7):4766-72.

Xu Y, Rivas JM, Brown EL, Liang X, Höök M. Virulence potential of the staphylococcal adhesin CNA in experimental arthritis is determined by its affinity for collagen. *J Infect Dis.* 2004;189(12):2323-33. Epub May 25, 2004.

Patti JM, Bremell T, Krajewska-Pietrasik D, Abdelnour A, Tarkowski A, Rydén C, Höök M. The *Staphylococcus aureus* collagen adhesin is a virulence determinant in experimental septic arthritis. *Infect Immun.* 1994 ;62(1):152-61.

Zong Y, Xu Y, Liang X, Keene DR, Höök A, Gurusiddappa S, Höök M, Narayana SV. A 'Collagen Hug' model for *Staphylococcus aureus* CNA binding to collagen. *EMBO J* 2005; 24(24):4224-36.

Ng K, Hsu H, Joh K, Inglis P, Torzilli P, Warren R, Maher S. Chondrocytes migrate into a novel macroporous polyvinyl alcohol scaffold in an in vitro cartilage defect model. *Trans Orthop Res Soc* 2010, 35:144.

Wann ER, Gurusiddappa S, Hook M. The fibronectin-binding MSCRAMM FnbpA of *Staphylococcus aureus* is a bifunctional protein that also binds to fibrinogen. *J Biol Chem.* 2000; 275(18):13863-71.

Dennes TJ, Schwartz J. A nanoscale adhesion layer to promote cell attachment on PEEK. *J Am Chem Soc* 2009; 131 (10):3456-57.

Bravenboer J, Maur CD, Bos PK, Feenstra L, Verhaar JA, Weinans H, Osch GJ. Improved cartilage integration and interfacial strength after enzymatic treatment in a cartilage transplantation model. *Arthritis Res Ther* 2004; 6(5):469-76.

Curl WW, Krome J, Gordon ES, Rushing J, Smith BP, Poehling GG. Cartilage injuries: a review of 31,516 arthroscopies. *Arthroscopy* 1997;13:456-460.

Kuo CK, Li WJ, Mauck RL, Tuan RS. Cartilage tissue engineering: Its potential and uses. *Curr Opin Rheumatol* 2006;18:64-73.

Williams RJ, Gamradt SC. Articular cartilage repair using a resorbable matrix scaffold. *Instr Course Lect* 2008; 57:563-71.

Vacanti CA, Langer R, Schloo B, Vacanti JP. Synthetic polymers seeded with chondrocytes provide a template for new cartilage formation. *Plast Reconstr Surg* 1991;88:753-9.

Cima LG, Vacanti JP, Vacanti C, et al. Tissue engineering by cell transplantation using degradable polymer substrates. *J Biomech Eng* 1991;113:143-51.

\* cited by examiner

COMPOSITION FOR THE ATTACHMENT OF IMPLANTS TO COLLAGEN OR OTHER COMPONENTS OF BIOLOGICAL TISSUE

CROSS REFERENCE TO RELATED APPLICATION

The present application claims priority to U.S. patent application Ser. No. 61/434,144, filed Jan. 19, 2011, which is hereby incorporated by reference in its entirety.

FIELD OF THE INVENTION

The present invention is in the field of implants, more specifically a composition in which an implant will attach to a component of the extracellular matrix in a biological tissue, in a short period of time after implantation into a subject. The present invention is also a method for use and manufacture of the composition as well as a novel use for the protein, CNA, derived from the collagen adhesion gene of *Staphylcoccus aureus*.

BACKGROUND OF THE INVENTION

Articular cartilage is a hydrated and lubricated joint tissue that allows for the relative movement of opposing joint surfaces under high loads (Buckwalter et al. (1998)). A sparse distribution of chondrocytes reside in the dense extracellular matrix of the tissue, with components such as collagen, proteoglycan and water inhomogenously dispersed through the depth of the tissue.

Mature articular cartilage does not possess an intrinsic ability to heal, since it is avascular and lacks a source of mesenchymal cells (Buckwalter et al. (1998)). Therefore, small focal cartilage defects can propagate unchecked to include the entire joint, eventually leading to osteoarthritis (OA) (Buckwalter et al. (1998)), a condition which affects as many as 27 million Americans with societal costs greater than $15 billion annually (Woolf et al. (2003): Gelber et al. (2000)). Current operative procedures for the treatment of articular cartilage damage generally fall into four categories: 1. nontransplant salvage operations such as abrasion arthroplasty; 2. mosaicplasty in which a cartilage-bone plug is transplanted into a joint which is minimally weight bearing; 3. reimplantation of autogenously isolated and expanded cells; and 4. the implantation of allografts (Maher et al. (2007); Szerb et al. (2005); Freedman et al. (2003); Brittburg et al. (2003); Gross (2003)). However, all of these techniques have their limitations, and do not prevent the progression of the osteoarthritis, which often propagates from the focal defect. Furthermore, over 33% of those affected by arthritis are under age 65. Accordingly, the number of young patients with total knee replacement, the end stage treatment for arthritis, is increasing. Performance of joint replacements in younger patient populations is less satisfactory than for older patients, oftentimes leading to multiple revision surgeries, each with successively diminishing longevity.

The problem with many of the surgical approaches and implantable materials that have been developed thus far, is the inability to integrate with the native tissue. For example, microfracture, the most commonly used clinical procedure for the treatment of full-thickness defects, results in poor integration between the fibrocartilage tissue that fills the defect site and the surrounding host tissue hyaline cartilage (Lane et al. (2010); Fortier et al. (2010); Gill et al. (2005); Hoemann et al. (2005); Watanabe et al. (2009); Hattori et al. (2008); LaPrade et al. (2008); Morisset et al. (2007); Kreuz et al. (2006)). Osteochondral autograft transfer is another technique developed to fill osteoarticular defects in weight bearing regions of the knee (Bobic (1996); Hangody et al. (1998)). However, chondrocyte death at the margins of the autograft (Evans et al. (2004); Zhang et al. (2005); Hunziker et al. (2003); Enders et al. (2010)) and persistent gaps between the graft and the host tissue (Kock et al. (2004); Lane et al. (2004); Williams et al. (2007); Marquass et al. (2010)) have been shown to lead to poor graft durability over time (Solheim et al. (2010)). In cases where implants are used to fill the defect, margin integration is frequently characterized by gaps and fissuring in histologic sections (Schafer et al. (2002); Niederauer et al. (2000); Wegener et al. (2010); Nehrer et al. (1998); Jiang et al. (2007); Ito et al. (2005); Wang et al. (2010)).

Efforts to create a mechanically stable interface between an implant and the host articular cartilage have explored the use of partial enzymatic digestion of the host tissue (Obradovic et al. (2001); Hunziker et al. (1998)) and the release of chemotactic agents to increase the number of matrix generating cells at the interface (Pabbruwe et al. (2009); Fortier et al. (2002)). Such approaches may help to reinforce the boundary between the scaffold and the host tissue as a function of time, but they do not address the problems associated with an initially unstable interface. Newer approaches rely on the use of an adhesive agent as an intermediary that chemically binds the native tissue to the implant in an attempt to immediately "glue" the scaffold to the surrounding native cartilage. One such example involves using a functionalized chondroitin sulphate paste to create a covalent bond between a biomaterial and proteins in articular cartilage (Wang et al. (2007); Strehin et al. (2010)). While the technology has been demonstrated to increase the interfacial strength and percent tissue fill in scaffold implanted cartilage defects, the addition of yet another interface (that between the glue and the implant and the implant and the cartilage) is far from ideal.

Therefore, there is a need in the art for a more reliable method to treat patients with focal defects, especially young active ones, early in the course of the problem, thus delaying or eliminating the need for total joint replacement, and a real need in the art for composition and method which increases focal strength and integration of an implant in a short period of time after implantation.

SUMMARY OF THE INVENTION

The present invention overcomes the problems in the art by providing for a novel composition comprising an implant, construct or scaffold to which a biological or chemical moiety is bound, such biological or chemical moiety having the ability to bind to a component of the extracellular matrix of the host tissue upon implantation. Upon implantation, the moiety of the composition would allow the implant to integrate with the extra-cellular matrix components of the host tissue in a short period of time.

In a preferred embodiment, the moiety would bond with collagen, thus, any tissue that contains collagen in its extra-cellular matrix is a candidate for implantation of the composition. In a preferred embodiment, the composition is suitable for implantation into a mammal, to treat, repair or replace defects and/or injury to musculoskeletal tissue including bone, tendon, ligaments, cartilage and the discs of the spine. In a preferred embodiment the implant is used to stabilize a chrondral defect, which is a defect in the articular cartilage at the end of the bones. In a most preferred embodiment, the chondral defect is found in the knee.

In a preferred embodiment, the moiety is chemical, and in a most preferred embodiment, contains a chemically reactive group, such as a carbonate ("open carbonate" or "OC").

In another preferred embodiment, the moiety is biological. Biological moieties would be derived from living organisms or through protein engineering, and could include, but are not limited to, proteins, protein sub-domains, and mutated proteins with altered affinity for a ligand, in particular, collagen. One source for biological moieties would be bacteria, including but not limited to *Staphylococcus aureus, Enterococcus faecalis*, and *Streptococcus mutans*. Other sources would be mammalian collagen binding proteins, such as decorin. A preferred biological moiety is a protein derived from *Staphylococcus aureus*, encoded by the collagen adhesion gene, CNA.

The implant, scaffold, or construct of the novel composition can be made of non-degradable, partially degradable, or fully degradable polymer. A preferred material for the implant is poly(vinyl) alcohol ("PVA"). It is also preferred that the implant be porous, and allow for and facilitate the migration of cells into the implant. The implant can also be fibrinogen or fibrin.

Another embodiment of the present invention is a method to manufacture the composition by functionalizing the implant with the moiety.

Another embodiment of the present invention is a method for the treatment, repair or replacement of biological tissue, in a subject in need thereof, by implantation of the composition. In a preferred embodiment, the biological tissue is musculoskeletal tissue.

Yet another embodiment of the present invention is a novel use for the CNA protein derived from *Staphylococcus aureus*. This novel use is based upon the ability of CNA to bind to collagen in tissue which contains collagen. This ability allows CNA to be used as a binder or connector between host tissue found in a subject and a foreign object or implant being used to treat or diagnose the subject.

Another embodiment of the present invention is a novel use for reactive organic carbonate (open carbonate) groups. Again, this novel use is based upon the ability of the reactive organic carbonate groups to bind to collagen or other amino group side chain-containing proteins or molecules in tissue. This ability allows the reactive organic carbonate groups to be used as a binder or connector between host tissue found in a subject and a foreign object or implant being used to treat or diagnose the subject.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 1(A) depicts Texas-Red labeled CNA attached to full thickness bovine articular cartilage as seen by the red fluorescence using fluorescent microscopy (red fluorescence). FIG. 1(B) depicts anti-hexahistidine tag antibodies bound to CNA detected with immunohistochemistry on bovine articular cartilage. FIGS. 1(C) and (D) show Texas-Red labeled CNA covalently bonded to the scaffold as seen by the red fluorescence using fluorescent microscopy.

FIG. 4(A) shows a PVA scaffold functionalized with CNA incubated with collagen in suspension, FIG. 4(B) shows a PVA scaffold functionalized with CNA but not incubated with collagen, and FIG. 4(C) shows a non-functionalized scaffold incubated with collagen.

DETAILED DESCRIPTION OF THE INVENTION

Figure 1:
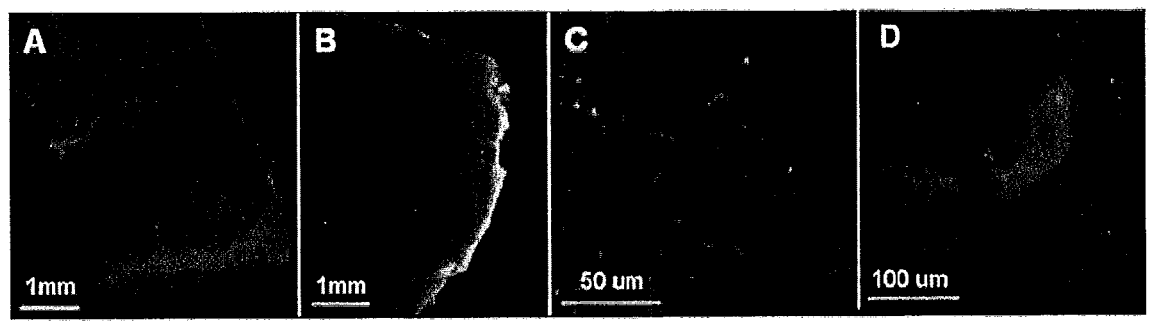
FIG. 1 are fluorescence microscopy images showing that CNA binds to cartilage (FIGS. 1(A) and 1(B)) and PVA scaffolds (FIGS. 1(C) and 1(D)).

The current invention is a novel composition comprising an implant, scaffold or construct bound to a biological or chemical moiety, which upon implantation into a subject, the moiety binds to a component of the extracellular matrix of the host tissue.

The current invention is also a method of manufacturing the novel composition.

The current invention is also a method of treating, repairing or replacing biological tissue, preferably musculoskeletal tissues, by implanting the biocompatible composition into a subject, in need thereof.

The current invention is also a method of using the bacterial protein encoded by the collagen adhesion gene of *Staphylococcus aureus*, known as CNA. The novel use of CNA is based upon its ability to bind to collagen in tissue which contains collagen. This ability allows CNA to be used as a binder or connector between host tissue found in a subject and a foreign object or implant being used to treat or diagnose the subject.

The current invention is also a method for using reactive organic carbonate (open carbonate) groups. Again, this novel use is based upon the ability of the reactive organic carbonate groups to bind to collagen or other amino group side chain-containing proteins or molecules in tissue. This ability allows the reactive organic carbonate groups to be used as a binder or connector between host tissue found in a subject and a foreign object or implant being used to treat or diagnose the subject.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "biocompatible" as used in the application means capable of coexistence with living tissues or organisms without causing harm.

The term "extracellular matrix" as used in the application means the substance of a tissue outside and between cells.

The term "moiety" as used in the application means part of a composition that exhibits a particular set of chemical and pharmacologic characteristics. "Biological moieties" are those which derive from living organisms or through protein engineering.

The terms "implant", "construct", and "scaffold" are used interchangeably throughout this application and means any material inserted or grafted into the body that maintains support and tissue contour.

The term "porous" as used in the application means having pores, which are defined as a minute opening.

The term "subject" as used in this application means an animal with an immune system such as avians and mammals. Mammals include canines, felines, rodents, bovines, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "in need thereof" would be a subject known or suspected of having an injury to or defect in any tissue, preferably musculoskeletal tissue, including but not limited to, cartilage, bone, tendon, ligaments, and the discs of the spine, and other tissues that contain collagen.

The terms "treat", "treatment", and the like refer to a means to slow down, relieve, ameliorate or alleviate at least one of the symptoms of the defect or injury or reverse the defect or injury after its onset.

A "chondral defect" is defined as a defect in the articular cartilage at the end of the bones.

The term "polymer" means a large molecule composed of repeating structural units often connected by covalent chemical bonds. Polymers can be natural or synthetic.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

Biological or Chemical Moiety

Microbial surface component recognizing adhesive matrix molecules or MSCRAMMs allow bacteria or other entities to attach to an extracellular matrix component in a tissue. *Staphylococcus aureus* is an aggressive bacterium that infects many tissues including cartilage. Its virulence is mediated by its ability to attach very strongly to collagen. The bacterium utilizes the MSCRAMM which is encoded by the CNA gene, known as the CollageN Adhesion protein or CNA (Mohamed et al. (1999); Switalski et al. (1989); Patti et al. (1992); Xu et al. (2004); Patti et al. (1994); Zong et al. (2005)).

CNA is a well characterized protein that has affinity for collagen type I, collagen type II (a major constituent of the extracellular matrix of articular cartilage), and collagen-like peptides (Switalski et al. (1989); Patti et al. (1992); Xu et al. (2004); Zong et al. (2005)). The full length CNA is approximately 135 kDal and contains an N-terminal signal sequence, an A region containing N1, N2, and N3 domains, B repeats, and a cell wall anchoring region. The CNA (CNA35) minimal binding region demonstrates the highest affinity for collagen (Xu et al. (2004); Zong et al. (2005)). CNA35 constitutes the N1 and N2 domains separated by a linker sequence with each domain exhibiting an IgG-like fold. Biochemical assays in combination with x-ray crystallography suggest a mechanism of binding where the N2 domain initiates contact with the collagen triple helix; subsequently the linker and N1 domain wrap around the helix using a so-called "hug mechanism" (Zong et al. (2005)).

Because CNA is well-characterized and has been successfully cloned, expressed using a vector in an *E. coli* host, and purified, there is an ability to mass produce purified recombinant CNA.

The current invention is based upon the strong binding affinity of CNA to collagen. One embodiment of the current invention is the novel use of the protein encoded by the CNA gene of *Staphylococcus aureus*. The CNA can be used as a binder or connector of host tissue found in a subject that contains collagen and a foreign object or implant being used to treat or diagnose the subject. While recombinant CNA has been extensively tested with collagen monomer fibers in suspension, its ability to bind to collagen in intact pieces of cartilage had not been tested to date. As shown in Example 2, recombinant CNA can bind to collagen in intact pieces of cartilage.

Another embodiment of the present invention involves attaching one end of CNA to the periphery of an implant, such that upon implantation, the other end can attach to collagen in articular cartilage, the implant would immediately attach to the collagen, preferably collagen II, in articular cartilage or any other tissue containing collagen.

As shown in Examples 4 and 5, implant-bound CNA can bind to collagen type II. Moreover, the implant-bound CNA increased the cartilage-implant interface strength at Day 0 as compared to implants functionalized with another protein, bovine serum albumin, and those unfunctionalized, without adversely affecting the ability of the cells to migrate into the scaffold (Example 6). There was no significant difference in the number of cells that migrated into the scaffold, in the amount of new matrix deposited, or in the histological appearance of the samples as a function of the treatment, suggesting that the presence of CNA does not have an adverse effect on chondrocyte migration. Because the CNA significantly increases the Day 0 interfacital strength between the implant and articular cartilage, without adversely affecting the cellular response, the CNA can be used to create a stable interface across which cells can migrate and lay down a matrix.

While CNA is the exemplified moiety, any chemical or biological moiety that has the ability to attach to collagen can be used. Examples of chemical moieties that could be used to bind collagen include, but are not limited to, organic carbonate, —OC(=O)O—. As shown in Example 4, implants functionalized with "open carbonate groups", where the reactive site remained free to interact with any amino group side chain-containing protein or molecule, also resulted in an ability to bind collagen type II. This also resulted in an increased interfacial strength at Days 0 and 21, with no change in the number of cells that migrated into the scaffold, in the amount of new matrix deposited, or in the histological appearance.

Biological moieties would be derived from living organisms or through protein engineering, and could include, but are not limited to, proteins, protein sub-domains, and mutated proteins with altered affinity for a ligand, in particular, collagen. One source for biological moieties would be bacteria, including but not limited to *Staphylococcus aureus, Enterococcus faecalis*, and *Streptococcus mutans*. Other sources would be mammalian collagen binding proteins, such as decorin. In one embodiment, proteins such as a MSCRAMM or CNA, can be attached to the polymer or implant directly.

Moreover, as would be understood by one of skill in the art, chemical and biological moieties can be used which have the ability to bind to another component of the extracellular matrix of the host tissue, other than collagen. Such components include, but are not limited to, fibronectin and laminin. Moieties that would have the ability to bind to these components, include, but are not limited to, FnBPA/B, BBK32, and Lmb.

It will also be understood by a person of skill in the art that the moieties can be modified to have an increased binding with collagen or another component of the extracellular matrix of the host tissue. With regard to biological moieties, especially recombinant proteins such as CNA, it is within the skill of those in the art to modify the protein via recombinant DNA or genetic engineering techniques in order to obtain a protein with increased binding activity.

Implants

Laboratory investigations and preclinical animal studies have most recently focused on the use of biodegradable matrix scaffolds, alone and in combination with chondrogenic cells, in order to improve the quality of cartilage repair tissue after surgery (Kuo et al. (2006)). Both natural and synthetic polymers have been fabricated for use as cell-seeded scaffolds, the chemistry and biology of which has taken a variety of forms, including fibrous structures, porous sponges, woven or non-woven meshes, and hydrogels (Kuo et al. (2006); Williams and Gamradt (2008); Vacanti et al. (1991); Cima et al. (1991)). Integration with the surrounding native cartilage remains a significant challenge for all implants. Thus, any implant, including but not limited to the ones referenced above, suitable for implantation into tissue, preferably musculoskeletal tissue, can be used in the composition. The implant can be made of non-degradable, partly degradable, or fully degradable natural or synthetic polymer depending upon the use and location of the implant. The implant can also contain other factors immobilized on the surface, such as those that support cell migration and/or matrix deposition, such as growth factors and chemoattractants. One of skill in the art can determine which type of polymer is best suited for the desired use and location of the implant.

One preferred implant is fibrinogen or fibrin.

Another preferred implant is made of poly(vinyl alcohol) or PVA. A preferred implant is also porous, and more preferably would allow the inward migration of cells. A porous PVA scaffold for the purposes of replacing, repairing or treating defects or injury in musculoskeletal tissue, preferably cartilage, has been described in U.S. patent application Ser. No. 13/349,365, incorporated herein by reference in its entirety. It has been shown that cells can migrate into and remain viable within the construct.

The implant or scaffold can be chemically modified so that the biological or chemical moiety capable of binding to the extracellular matrix of the host cell can become attached to the implant, providing immediate attachment between the implant and the host tissue. In a preferred embodiment, the protein, CNA, can be attached to a PVA implant. When implanted, the CNA will adhere to the exposed fibrillar collagen type II in the cartilage and provide immediate attachment between the implant and articular cartilage. The porous PVA implant will readily accept the inward migration of cells to further enhance integration, but the initial adhesion between the implant and cartilage is not contingent upon the cell migration. Another preferred embodiment, carbonate groups are attached to a PVA implant, and supply the same immediate attachment between the implant and articular cartilage.

CNA was attached to the previously described PVA scaffold using a novel method to insure that the protein would be anchored using the N-terminus. This type of anchoring will not interfere with the CNA ability to bind to collagen. The PVA implant is chemically modified or functionalized to have the CNA protein or open carbonate attached by the sequence of steps set forth in FIG. 2 and described in detail in Example 2. One of skill in the art can easily modify the method in order to obtain an implant with any biological or chemical moiety that binds to a host tissue. In particular, the R group shown in FIG. 2, (5) and (6), can be changed to attach the desired chemical or biological moiety using standard methods of organic synthesis. The adhesion layer used to bond the OC can be applied to any organic or inorganic polymer that contains O, N, or S ligating groups.

Use of the Composition

The composition comprising an implant, construct or scaffold to which a chemical or biological moiety is bound of the current invention can be used to treat, replace or repair defects and/or injuries in various tissues, in a subject in need thereof, preferably a mammal, and most preferably a human. In a preferred embodiment, the tissue would contain collagen in the extracellular matrix and most preferably is musculoskeletal tissue. Musculoskeletal tissue contemplated to be treated, replaced or repaired includes bone, tendon, ligaments, cartilage and the discs of the spine. In a preferred embodiment, the biocompatible composition is used to replace focal defects in articular cartilage. In a most preferred embodiment, the defect is found in the knee. The biocompatible composition, due to the chemical or biological moiety, attaches immediately to the host tissue, and provides increased interfacial strength to the implant immediately upon implantation. In a preferred embodiment, the implant allows for the migration of cells into the implantation site, allowing for continued increase in strength.

Those of skill in the art would appreciate that the implants, constructs or scaffolds of the present invention may be implanted into a subject using operative techniques and procedures, utilizing such techniques as magnetic resonance imaging and computer guided technology. One of skill in the art would also appreciate that the tissue of the subject can be pre-treated prior to implantation with any agent that would expose the collagen or other component of the extracellular matrix to which the biological or chemical moiety is desired to bind.

EXAMPLES

The present invention may be better understood by reference to the following non-limiting examples, which are presented in order to more fully illustrate the preferred embodiments of the invention. They should in no way be construed to limit the broad scope of the invention.

Example 1

General Materials and Methods

Expression and Purification of Recombinant CNA

The recombinant protein CNA35 was cloned into pQE30 expression plasmid and transformed into *E. coli* as previously described (Zong et al. (2005)). Expression and purification of recombinant CNA was performed as previously described (Wann et al. (2000)). Briefly, bacterial lysates expressing an N-terminal-hexa-histadine tagged CNA were first purified by nickel chelate affinity chromatography using a 5-ml Hi-Trap chelating column in a fast protein liquid chromatography system (Amersham BioSciences, GE). Fractions, collected and analyzed by SDS-PAGE, containing protein of expected size, were pooled and dialyzed in 25 mM Tris-HCl, pH 8 and further purified in a 5 ml Hi-Trap Q-Sepharose column (Amersham Biosciences, GE) using a linear gradient of 0 to 1M NaCl.

Porous Polyvinyl Alcohol (PVA) Scaffolds

Porous polyvinyl alcohol (PVA) scaffolds were manufactured using the method described in U.S. patent application Ser. No. 13/349,365, which is incorporated herein by reference in its entirety. In brief, rectangular collagen sponges were impregnated with 10% weight PVA in solution with deionized water and the construct was subjected to six freeze-thaw cycles over a period of five days. The impregnated sponges were cored into cylindrical geometries using a 5 mm diameter biopsy punch, and sliced to the desired height to form cylinders. The cylindrical specimens were digested with a collagenase solution to remove the collagen sponge and result in an interconnected porous PVA scaffold.

Statistical Analyses

Statistical analyses were performed using Graphpad Prism software. To test for significance, a 2-way ANOVA analysis was conducted with a post-hoc Bonferroni post-test. The two independent variables used were time (0 vs 21 days) and treatment type (BSA, CNA, UC, OC).

Example 2

Recombinant CNA can Bind Collagen Found in Intact Cartilage Tissue

Materials and Methods

Recombinant CNA as described in Example 1 was labeled with a fluorescent Texas-Red label as follows: CNA protein (2 mg/ml) was first dialyzed in NaHCO3 to 100 mM final concentration (pH 8.2). The CNA protein (5 ml) was incubated with Texas-Red dye (dissolved in DMF to 5 µg/µl) for 1 hour at room temperature in a shaker covered in aluminum foil. After the labeling reaction, the protein was dialyzed four times in 2 L phosphate buffered saline (PBS) buffer. Thin strips of articular cartilage approximately 1-2 mm thick (n=3) were isolated from juvenile bovine knees, incubated with Texas-Red tagged CNA, suspended in water at a concentration of 1 mg/mL for one hour with agitation, and washed vigorously. Three samples were examined with fluorescence microscopy.

Three additional articular cartilage samples were incubated with CNA (without a Texas-Red tag), suspended in water at a concentration of 1 mg/mL for one hour with agitation, washed, fixed, paraffin embedded, and immunohistochemistry was performed using an antibody to the polyhistidine tag on the CNA (Alpha Diagnostic, TX).

Results

After one hour of incubation in the presence of Texas-Red labeled CNA, the protein was detected on the edges of articular cartilage using fluorescent microscopy (FIG. 1(A)). The non-tagged CNA was also detected on the surface of the articular cartilage using immunohistochemistry with anti-hexa-histidine tag antibodies (FIG. 1(B)).

Example 3

PVA Scaffolds can be Functionalized with CNA

Materials and Methods

Interconnected polyvinyl alcohol (PVA) implants described in Example 1, were functionalized using a sequential process resulting in reactive carbonate groups on the scaffold's surface, which can covalently bond with any amino group (Dennes et al. (2009)). The procedure is summarized in FIG. 2 and the various processing steps are labeled from 1 to 6.

PVA implants were lyophilized for 24 hours to remove all water without collapsing the porous structure. They were then exposed to vapor of zirconium tetra(tert-butoxide) (FIG. 2, (1)) as previously described to create the interface (Dennes et al. (2009); U.S. Application Publ. No. 2009/0104474). The reaction chamber was then heated to 45° C. and was held at this temperature for 10 minutes. The chamber was back-filled with zero grade nitrogen, and the implant samples were then agitated to expose any surface that had not yet been coated. The newly exposed surfaces were then treated further with vapor of zirconium tetra(tert-butoxide) to create the interface between the implant and the phosphonic acid (Dennes et al. (2009); U.S. Application Publ. No. 2009/0104474).

Figure 2:
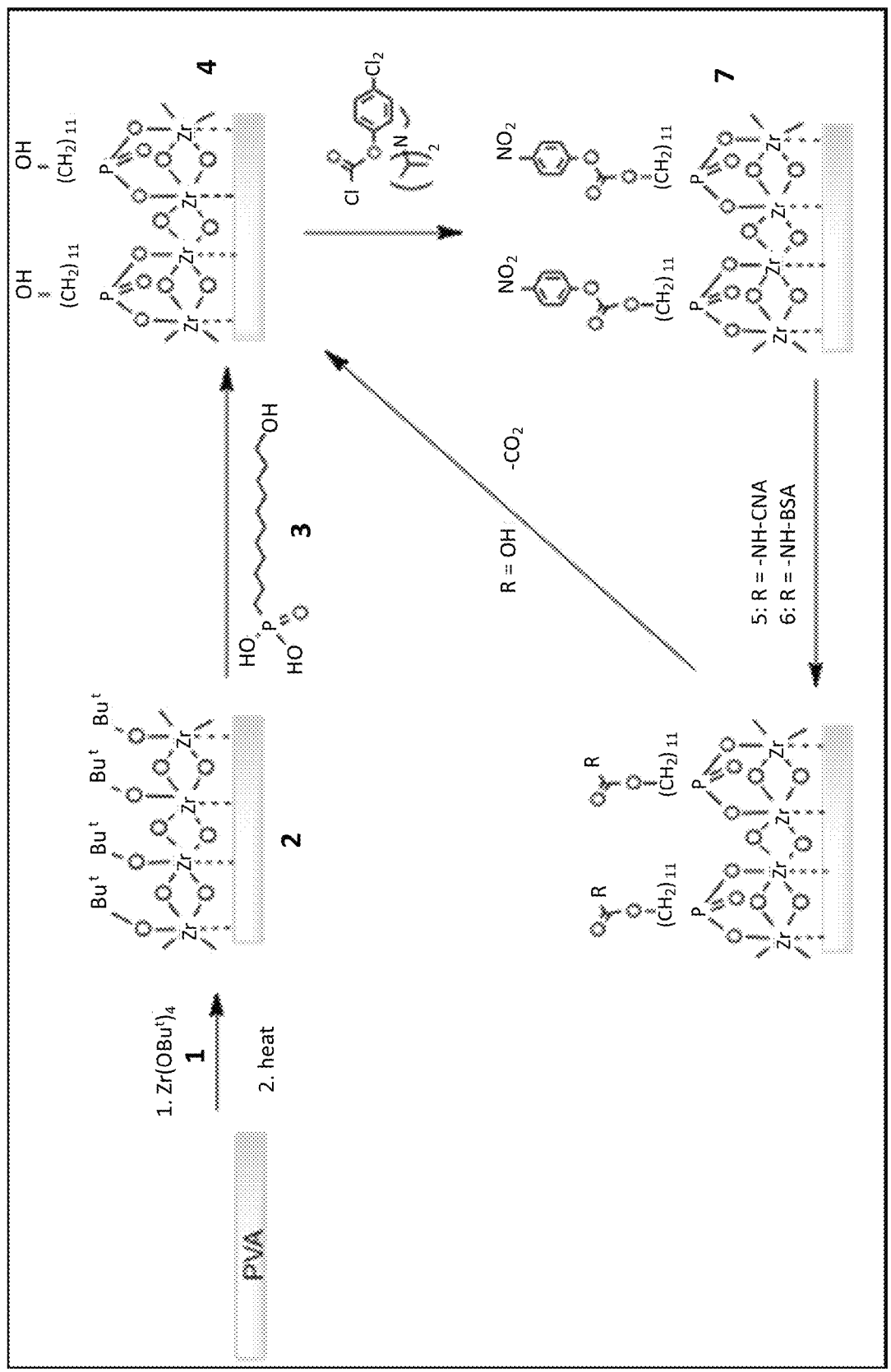
FIG. 2 is a representation of the series of steps required to functionalize the scaffolds.

The chamber was again heated to 45° C., and was held at this temperature for 10 minutes (FIG. 2, (2)). The chamber was again back-filled with zero grade N2, and the implants were quickly transferred into a 0.1 mM solution of 11-phosphonoundecanol (FIG. 2, (3)) in ethanol. After 12 hours the implants were removed from this solution, sonicated in ethanol, and dried in vacuo to give the surface-bound hydroxyalkylphosphonate. p-Nitrophenyl chloroformate (80 mg, 0.4 mmol) was dissolved under argon in 60 mL dry tetrahydrofuran in a 100 mL three-necked round bottom flask equipped with a dry stir bar and the activated implants (FIG. 2, (4)) were then submerged in the solution. Dry diisopropylethylamine (0.75 mL, 4 mmol) was added, and the suspension was stirred for 45 minutes. The implants were removed from this suspension and washed briefly with ethanol. These steps resulted in an implant functionalized with a group (called "open carbonates" or "OC") that can react with any nucleophile in solution.

The implants were then soaked in a solution of CNA in water (pH 8.5) for 24 hours (FIG. 2, (5)), or BSA in water (FIG. 2, (6)), or not soaked at all. All samples were removed from the solution and washed sequentially with water and ethanol.

These steps resulted in the following groups:
(i) an organophosphonate terminated with CNA (CNA);
(ii) the same phosphonate terminated with Bovine Serum Albumin (BSA), used as a control for functionalizing with a protein;
(iii) the organophosphonate terminated with organic carbonate groups that are free to react with any nucleophile in solution (called "open carbonates," OC);

and, (iv) untreated control (UC)

Three samples functionalized with Texas-Red labeled CNA were frozen sectioned and imaged using fluorescent microscopy.

Results

As shown in FIGS. 1(C) and 1(D), all the PVA scaffolds that were functionalized with Texas-Red labeled CNA, were found to have florescent edges indicating that the process successfully bound CNA to the walls of the scaffold.

Example 4

The Functionalized PVA Scaffolds can Bind Collagen

Materials and Methods

The PVA scaffolds (five from each of groups (i), (ii), (iii), and (iv), as described in Example 3), were incubated for three hours with a solution of collagen type II isolated from bovine articular cartilage and labeled with FITC (Sigma, Mo.) at 0.25 mg/mL. Each scaffold was washed with three centrifugation steps, frozen sectioned and imaged using fluorescence microscopy. Scaffolds that were not incubated with the collagen were also imaged to ensure that there was no autofluorescence. Images were captured using a microscope with exposure time consistent between groups by a blinded observer.

Results

Figure 3:
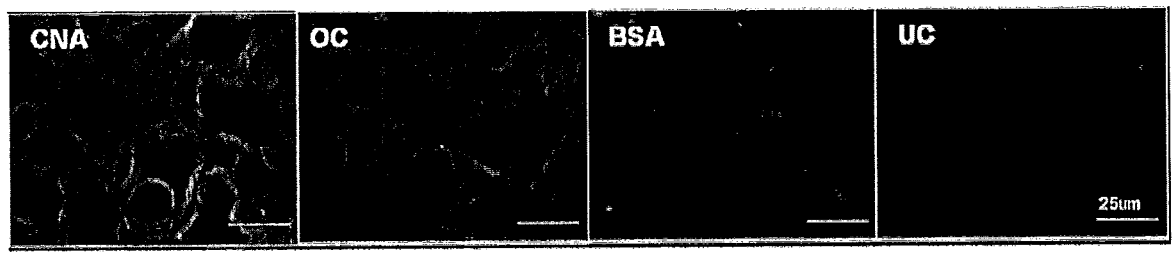
FIG. 3 shows fluorescence microscopy images of FITC-labeled collagen II incubated with PVA scaffolds functionalized with CNA, OC (open carbonate), BSA (bovine serum albumin), and UC (untreated). The presence of collagen II is only detected on the CNA and OC scaffolds, indicating that those two scaffolds have the ability to bind collagen.

The CNA-functionalized group of scaffolds bound collagen type II as demonstrated by a qualitative detection of the FITC tag on the collagen via fluorescence microscopy (FIG. 3). This result indicates that the processing steps to which the scaffold and CNA were subjected (Example 3) did not interfere with the ability of CNA to bind collagen. Surprisingly, the OC group also demonstrated an ability to bind collagen type II. The UC and BSA groups did not bind collagen (FIG. 3).

Example 5

Further Proof that the Funtionalized PVA Scaffolds can Bind to Collagen

Material and Methods

The PVA scaffolds functionalized in Example 3 were incubated in a solution of collagen type II isolated from bovine articular cartilage in phosphate buffered saline (PBS) for 4 hours. The scaffolds were removed from solution, vigorously washed in PBS, and stained with PicroSirius Red (Polysciences Inc., Warrington, Pa.), which stains collagen red. The samples were then fixed, paraffin embedded, sliced, and examined under a microscope.

Results

Figure 4:
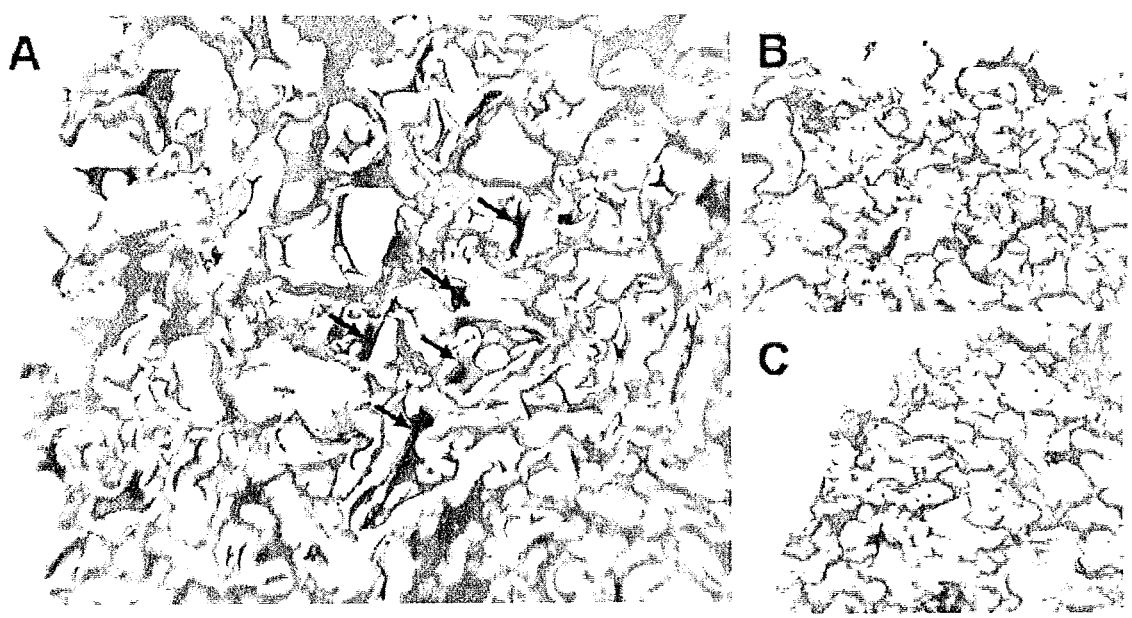
FIG. 4 shows images of PicroSirius staining of PVA scaffolds.

As shown in FIG. 4, the CNA functionalized PVA implant incubated with collagen is stained red by the PicroSirius Red (FIG. 4(A)). The CNA functionalized implant not incubated with collagen (FIG. 4(B)) and a non-functionalized PVA implant incubated with collagen (FIG. 4(C)) are not stained by the PicroSirius Red, showing that only the PVA implant functionalized with CNA bound to the collagen.

Example 6

Binding Strength of Functionalized PVA Scaffolds and Cartilage at Day 0

Materials and Methods

Figure 5:
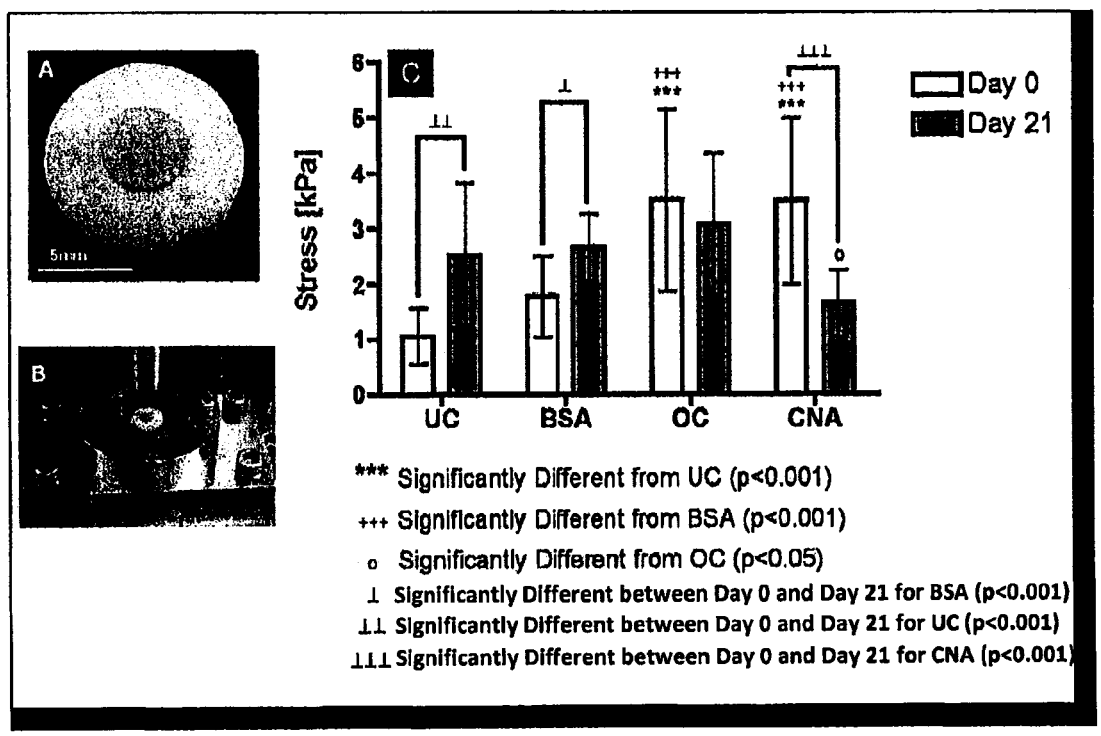
FIG. 5(A) shows an example of a bovine articular cartilage discs which were biopsy punched forming a central cylindrical 3.5 mm defect. A 5 mm diameter scaffold was press-fitted into the central defect.
FIG. 5(B) shows the push-out test set-up.
FIG. 5(C) is a graph of the interface strength of each group of functionalized scaffolds (UC, BSA, OC, and CNA), at Day 0 and Day 21.

Middle zone cartilage discs were isolated from juvenile bovine knees (10 mm diameter, 2 mm thick) and perforated in the center with a 3.5 mm diameter biopsy punch. Porous PVA scaffolds with a 5 mm diameter functionalized with CNA, BSA, OC, or US, as described in Example 3 (n=20 per group) were press fit into the central hole of the cartilage explants as shown in FIG. 5(A). Each bovine cartilage disc with the implant was incubated for four (4) hours at 37° C. in culture media and then subject to a push-out test.

To perform the push-out test, each sample was mounted on the base of a custom-built testing machine (as shown in FIG. 5(B)) and a stainless steel indenter used to push on the implant at a rate of 0.01 mm/s until the implant was completely pushed out of the cartilage ring (Bravenboer et al. (2004)). The maximum load was recorded and normalized to the surface area of the interface for each sample to compute maximum stress.

Results

As shown in FIG. 5(C), the interface strength on Day 0 was approximately three times higher for the implants from the CNA and OC groups than the BSA and UC groups. These differences were statistically significant. There is no significant difference between the push-out strength of the CNA and OC groups or between the BSA and UC groups.

Example 7

Interfacial Strength of PVA Scaffolds and Cartilage and Biocompatibility at Day 21

Materials and Methods

An additional 13 scaffold-cartilage constructs per group were cultured in 30 mL ADMEM/F12 with 100 nM dexamethasone, 50 µg/mL ascorbate-2-phosphate, and antibiotics (Sigma Aldrich) for 21 days, after which they were subjected to a push-out test where the maximum load was recorded. The scaffolds were digested using proteinase K (Sigma, Mo.), and assessed for glycosaminoglycan (GAG) content using a dimethylmethylene blue assay (DMMB) and DNA content using a quant-iT kit Pico green assay (Invitrogen, Calif.).

Results

As also shown in FIG. 5(C), on Day 21, the interface strength of the BSA was significantly higher than that of the CNA group. There was also a significant decrease in the push-out strength of the interface of the CNA group compared to the OC group. The BSA group had significantly higher push-out strength on Day 21 versus that of the CNA group. Also on Day 21, there was a significant decrease in the push out strength of the interface of the CNA group compared to that of the OC group.

Figure 6:
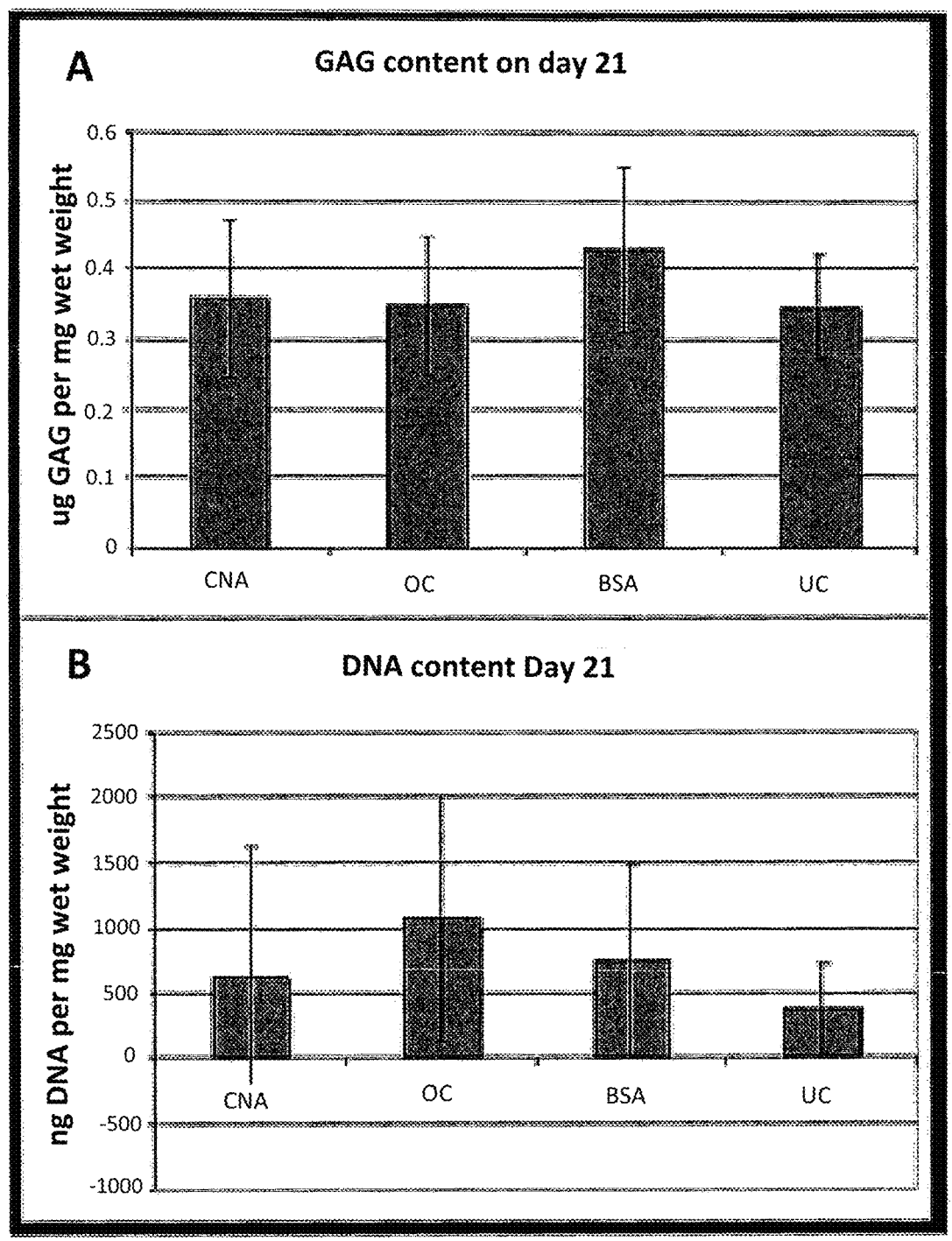
FIG. 6(A) is a graph depicting the GAG content as measured by DMMB assay and normalized to the wet weight of the scaffold, for each group of functionalized scaffolds (UC, BSA, OC, and CNA) at Day 21.
FIG. 6(B) is a graph depicting the DNA content as measured by a pico-green assay and normalized to the wet weight of the scaffold, for each group of functionalized scaffolds (UC, BSA, OC, and CNA) at Day 21.

There were no significant differences in GAG (FIG. 6(A)) content, or DNA content (FIG. 6(B)) after 21 days of incubation between the groups.

REFERENCES

Buckwalter J A, Mankin H J. Articular cartilage: degeneration and osteoarthritis, repair, regeneration, and transplantation. *Instr Course Lect* 1998; 47:487-504.

Woolf A D, Pfleger B. Burden of major musculoskeletal conditions. Bull World Health Organ 2003; 81(9):646-56.

Gelber A, Hochberg M, Mead L, Wang N, Wigley F, Klag M. Joint injury in young adults and risk for subsequent knee and hip osteoarthritis. *Ann Intern Med* 2000; 133(5):321-328.

Maher et al. Nondegradable Hydrogels for the Treatment of Focal Cartilage Defects, *J Biomed Mater Res* 2007; 83(A): 145.

Szerb et al. Mosaicplasty: Long-term Follow-up, *Bull Hosp. Jt. Dis.* 2005; 56:54.

Freedman et al. Marrow Stimulation Technique to Augment Meniscus Repair, *Arthroscopy* 2003; 19:794.

Brittberg et al. Articular Cartilage Engineering with Autologous Chrondrocyte Transplantation: A Review of Recent Developments, *J. Bone Joint Surg Am* 2003; 85(Supp3): 109.

Gross et al. Cartilage Resurfacing: Filling Defects, *J. Arthroplasty* 2003; 18 (3 Suppl. 1):14.

Lane J G, Healey R M, Chen A C, Sah R L, Amiel D. Can osteochondral grafting be augmented with microfracture in an extended-size lesion of articular cartilage? *Am J Sports Med* 2010; 38(7):1316-23.

Fortier L A, Potter H G, Rickey E J, Schnabel L V, Foo L F, Chong L R, Stokol T, Cheetham J, Nixon A J. Concentrated bone marrow aspirate improves full-thickness cartilage repair compared with microfracture in the equine model. *J Bone Joint Surg Am* 2010; 92(10):1927-37.

Gill T J, McCulloch P C, Glasson S S, Blanchet T, Morris E A. Chondral defect repair after the microfracture procedure: a nonhuman primate model. *Am J Sports Med* 2005; 33(5): 680-5.

Hoemann C D, Hurtig M, Rossomacha E, Sun J, Chevrier A, Shive M S, Buschmann M D. Chitosan-glycerol phosphate/blood implants improve hyaline cartilage repair in ovine microfracture defects. *J Bone Joint Surg Am* 2005; 87(12):2671-86.

Watanabe A, Boesch C, Anderson S E, Brehm W, Mainil Varlet P. Ability of dGEMRIC and T2 mapping to evaluate cartilage repair after microfracture: a goat study. *Osteoarthritis Cartilage* 2009; 17(10):1341-9.

Hattori K, Uematsu K, Matsumori H, Dohi Y, Takakura Y, Ohgushi H. Spectrocolorimetric evaluation of repaired articular cartilage after a microfracture. *BMC Res Notes* 2008; 1:87.

LaPrade R F, Bursch L S, Olson E J, Havlas V, Carlson C S. Histologic and immunohistochemical characteristics of failed articular cartilage resurfacing procedures for osteochondritis of the knee: a case series. *Am J Sports Med* 2008; 36(2):360-8.

Morisset S, Frisbie D D, Robbins P D, Nixon A J, McIlwraith C W. IL-1/IGF-1 gene therapy modulates repair of microfractured chondral defects. *Clin Orthop Relat Res* 2007; 462:221-8.

Kreuz P C, Steinwachs M R, Erggelet C, Krause S J, Konrad G, Uhl M, Stidkamp N. Results after microfracture of full-thickness chondral defects in different compartments in the knee. *Osteoarthritis Cartilage* 2006; 14(11):1119-25.

Bobić V. Arthroscopic osteochondral autograft transplantation in anterior cruciate ligament reconstruction: a preliminary clinical study. *Knee Surg Sports Traumatol Arthrosc* 1996; 3(4):262-4.

Hangody L, Kish G, Kárpáti Z, Udvarheyli I, Szigeti I, Bélay M. Mosaicplasty for the treatment of articular cartilage defects: application in clinical practice. *Orthopedics* 1998; 21(7):751-6.

Evans P J, Miniaci A, Hurtig M B. Manual punch versus power harvesting of osteochondral grafts. *Arthroscopy* 2004; 20(3):306-10.

Zhang Z, McCaffery J M, Spencer R G, Francomano C A. Growth and integration of neocartilage with native cartilage in vitro. *J Orthop Res* 2005; 23(2):433-9.

Hunziker E B, Quinn T M. Surgical removal of articular cartilage leads to loss of chondrocytes from cartilage bordering the wound edge. *J Bone Joint Surg Am* 2003; 85-A Suppl 2:85-92.

Enders J T, Otto T J, Peters H C, Wu J, Hardouin S, Moed B R, Zhang Z. A model for studying human articular cartilage integration in vitro. *J Biomed Mater Res A* 2010; 94(2): 509-14.

Kock N, van Susante J, Wymenga A, Buma P. Histological evaluation of a mosaicplasty of the femoral condyle-retrieval specimens obtained after total knee arthroplasty—a case report. *Acta Orthop Scand* 2004; 75(4):505-8.

Lane J G, Massie J B, Ball S T, Amiel M E, Chen A C, Bae W C, Sah R L, Amiel D. Follow-up of osteochondral plug transfers in a goat model: a 6-month study. *Am J Sports Med* 2004; 32(6):1440-50.

Williams R J, Ranawat A S, Potter H G, Carter T, Warren R F. Fresh stored allografts for the treatment of osteochondral defects of the knee. *J Bone Joint Surg Am* 2007; 89(4):718-26

Marquass B, Somerson J S, Hepp P, Aigner T, Schwan S, Bader A, Josten C, Zscharnack M, Schulz R M. A novel MSC-seeded triphasic construct for the repair of osteochondral defects. *J Orthop Res* 2010; 28(12):1586-99.

Solheim E, Hegna J, Oyen J, Austgulen O K, Harlem T, Strand T. Osteochondral autografting (mosaicplasty) in articular cartilage defects in the knee: results at 5 to 9 years. *Knee* 2010; 17(1):84-7.

Schaefer D, Martin I, Jundt G, et al. Tissue-engineered composites for the repair of large osteochondral defects. *Arthritis Rheum* 2002; 46(9):2524-34.

Niederauer G G, Slivka M A, Leatherbury N C, et al. Evaluation of multiphase implants for repair of focal osteochondral defects in goats. *Biomaterials* 2000; 21(24):2561-74.

Wegener B, Schrimpf F M, Bergschmidt P, et al. Cartilage regeneration by bone marrow cells-seeded scaffolds. *J Biomed Mater Res A* 2010; 95(3):735-40.

Nehrer S, Breinan H A, Ramappa A, et al. Chondrocyte-seeded collagen matrices implanted in a chondral defect in a canine model. *Biomaterials* 1998; 19(24):2313-28

Jiang C C, Chiang H, Liao C J, et al. Repair of porcine articular cartilage defect with a biphasic osteochondral composite. *J Orthop Res* 2007; 25(10):1277-90.

Ito Y, Ochi M, Adachi N, et al. Repair of osteochondral defect with tissue-engineered chondral plug in a rabbit model. *Arthroscopy* 2005; 21(10):1155-63

Wang W, Li B, Li Y, et al. In vivo restoration of full-thickness cartilage defects by poly(lactide-co-glycolide) sponges filled with fibrin gel, bone marrow mesenchymal stem cells and DNA complexes. *Biomaterials* 2010; 31(23):5953-65.

Obradovic B, Martin I, Padera R F, et al. Integration of engineered cartilage. *J Orthop Res* 2001; 19(6):1089-97.

Hunziker E B, Kapfinger E. Removal of proteoglycans from the surface of defects in articular cartilage transiently enhances coverage by repair cells. *J Bone Joint Surg Br* 1998; 80(1):144-50.

Pabbruwe M B, Esfandiari E, Kafienah W, Tarlton J F, Hollander A P. Induction of cartilage integration by a chondrocyte/collagen-scaffold implant. *Biomaterials* 2009; 30(26):4277-86.

Fortier L A, Insulin-like growth factor-1 enhances cell-based repair of articular cartilage. *J Bone Joint Surg Br* 2002; 84(2):276-88.

Sellers R S, Zhang R, Glasson S S, et al. Repair of articular cartilage defects one year after treatment with recombinant human bone morphogenetic protein-2 (rhBMP-2). *J Bone Joint Surg Am* 2000; 82(2):151-60.

Wang D A, Varghese S, Sharma B, Strehin I, Fermanian S, Gorham J, Fairbrother D H, Cascio B, Elisseeff J H. Multifunctional chondroitin sulphate for cartilage tissue biomaterial integration. *Nat Mater* 2007; 6(5):385-92.

Strehin I, Nahas Z, Arora K, Nguyen T, Elisseeff J. A versatile pH sensitive chondroitin sulfate-PEG tissue adhesive and hydrogel. *Biomaterials* 2010; 31(10):2788-97

Mohamed N, Teeters M A, Patti J M, Höök M, Ross J M Inhibition of *Staphylococcus aureus* adherence to collagen under dynamic conditions. *Infect Immun.* 1999 February; 67(2):589-94.

Switalski L M, Speziale P, Höök M. Isolation and characterization of a putative collagen receptor from *Staphylococcus aureus* strain Cowan 1. *J Biol Chem.* 1989 Dec. 15; 264(35):21080-6.

Patti J M, Jonsson H, Guss B, Switalski L M, Wiberg K, Lindberg M, Höök M. Molecular characterization and expression of a gene encoding a *Staphylococcus aureus* collagen adhesion. *J Biol Chem.* 1992 Mar. 5; 267(7):4766-72.

Xu Y, Rivas J M, Brown E L, Liang X, Höök M. Virulence potential of the staphylococcal adhesin CNA in experimental arthritis is determined by its affinity for collagen. *J Infect Dis.* 2004 Jun. 15; 189(12):2323-33. Epub 2004 May 25.

Patti J M, Bremell T, Krajewska-Pietrasik D, Abdelnour A, Tarkowski A, Rydén C, Höök M. The *Staphylococcus aureus* collagen adhesin is a virulence determinant in experimental septic arthritis. *Infect Immun.* 1994 January; 62(1):152-61.

Zong Y, Xu Y, Liang X, Keene D R, Höök A, Gurusiddappa S, Höök M, Narayana S V. A 'Collagen Hug' model for *Staphylococcus aureus* CNA binding to collagen. *EMBO J* 2005; 24(24):4224-36.

Ng K, Hsu H, Joh K, Inglis P, Torzilli P, Warren R, Maher S. Chondrocytes migrate into a novel macroporous polyvinyl alcohol scaffold in an in vitro cartilage defect model. *Trans Orthop Res Soc* 2010, 35:144.

Wann E R, Gurusiddappa S, Hook M. The fibronectin-binding MSCRAMM FnbpA of *Staphylococcus aureus* is a bifunctional protein that also binds to fibrinogen. J Biol Chem. 2000 May 5; 275(18):13863-71.

Dennes T J, Schwartz J. A nanoscale adhesion layer to promote cell attachment on PEEK. *J Am Chem Soc* 2009; 131 (10):3456-57.

Bravenboer J, Maur C D, Bos P K, Feenstra L, Verhaar J A, Weinans H, Osch G J. Improved cartilage integration and interfacial strength after enzymatic treatment in a cartilage transplantation model. *Arthritis Res Ther* 2004; 6(5):469-76.

Curl W W, Krome J, Gordon E S, Rushing J, Smith B P, Poehling G G. Cartilage injuries: a review of 31,516 arthroscopies. *Arthroscopy* 1997; 13:456-460.

Kuo C K, Li W J, Mauck R L, Tuan R S. Cartilage tissue engineering: Its potential and uses. *Curr Opin Rheumatol* 2006; 18:64-73.

Williams R J, Gamradt S C. Articular cartilage repair using a resorbable matrix scaffold. *Instr Course Lect* 2008; 57:563-71.

Vacanti C A, Langer R, Schloo B, Vacanti J P. Synthetic polymers seeded with chondrocytes provide a template for new cartilage formation. *Plast Reconstr Surg* 1991; 88:753-9.

Cima L G, Vacanti J P, Vacanti C, et al. Tissue engineering by cell transplantation using degradable polymer substrates. *J Biomech Eng* 1991; 113:143-51.

The invention claimed is:

1. A composition comprising an implant and a biological moiety comprising a bacterial microbial surface component recognizing adhesive matrix molecules (MSCRAMM) or a reactive organic carbonate chemical moiety, wherein the biological or chemical moiety is bound to the implant and has the ability to bind to a component of the extracellular matrix of a biological tissue, whereby the implant and the biological tissue become attached upon introduction of the composition to biological tissue.

2. The composition of claim 1, wherein the biological moiety is a protein, protein sub-domain or mutated protein.

3. The composition of claim 2, wherein the protein is a mammalian collagen binding protein.

4. The composition of claim 2, wherein the protein is derived from *Staphylococcus aureus, Enterococcus faecalis*, or *Streptococcus mutans*.

5. The composition of claim 4, wherein the protein is S. aureus collagen adhesin (CNA) protein.

6. The composition of claim 1, wherein the component of the extracellular matrix is collagen.

7. The composition of claim 1, wherein the biological tissue is musculoskeletal tissue.

8. The composition of claim 1, wherein the implant is comprised of a non-biodegradable, partly degradable or fully degradable polymer.

9. The composition of claim 1, wherein the implant is comprised of poly(vinyl) alcohol.

10. The composition of claim 1, wherein the implant is porous.

11. The composition of claim 1, wherein the implant allows for the migration of cells into the implant.

12. The composition of claim 1, wherein the implant is fibrin or fibrinogen.

13. The composition of claim 1, further comprising a growth factor or chemoattractant.

14. A method of using the composition of claim 1 for the treatment, repair or replacement of cartilage, by implantation of the composition of claim 1 into a subject in need thereof.

15. The method of claim 14, wherein the subject is a mammal.

16. The method of claim 15, wherein the mammal is a human.

17. A method for the manufacture of the composition comprising an implant and a biological moiety, comprising a bacterial MSCRAMM, or a reactive organic carbonate chemical moiety of claim 1, comprising the steps of:
   a. lyophilizing the implant for a period of time sufficient to remove all of the water from the implant without collapsing the porous structure;
   b. exposing the implant to a vapor of zirconium tetra(tert-butoxide);
   c. heating the implant;
   d. agitating the implant in the presence of zero grade nitrogen;
   e. re-exposing the implant to a vapor of zirconium tetra (tert-butoxide);
   f. heating and agitating the implant in the presence of zero grade nitrogen;
   g. exposing the implant to 11-phosphonoundecanol;
   h. submerging the implant in p-nitrophenyl chloroformate dissolved in tetrahydrofuran;
   i. adding diisopropylethylamine to the solution containing the implant; and
   j. removing the implant;
   wherein the resulting composition comprises the implant and a reactive organic carbonate bound to the implant.

18. The method of claim 17, further comprising the step of soaking the implant in a solution of a biological moiety comprising a bacterial MSCRAMM for a period of time sufficient for the biological moiety comprising a bacterial MSCRAMM to bind to the implant.

19. The composition of claim 2, wherein the protein, protein sub-domain or mutated protein has an increased ability to bind to the component of the extracellular matrix of the biological tissue.

* * * * *